United States Patent [19]

Garska et al.

[11] Patent Number: 4,499,315
[45] Date of Patent: Feb. 12, 1985

[54] CONVERSION OF CERTAIN HYDROCARBONS USING SILICOALUMINOPHOSPHATE CATALYSTS

[75] Inventors: Daniel C. Garska, St. Albans, W. Va.; Brent M. Lok, New City, N.Y.

[73] Assignee: Union Carbide Corporation, Danbury, Conn.

[21] Appl. No.: 551,887

[22] Filed: Nov. 15, 1983

[51] Int. Cl.³ .................................................. C07C 3/00
[52] U.S. Cl. .................................... 585/415; 585/322; 585/513; 585/514; 585/528; 208/70; 208/135
[58] Field of Search ............... 585/415, 322, 513, 514, 585/527, 528; 208/70, 135

[56] References Cited

U.S. PATENT DOCUMENTS

| | | | |
|---|---|---|---|
| 2,507,625 | 5/1950 | Ehrhardt | 502/214 |
| 3,271,299 | 9/1966 | Kearby | 585/640 |
| 3,342,750 | 9/1967 | Kearby | 502/208 |
| 3,657,150 | 4/1972 | Juguin et al. | 585/671 |
| 4,132,669 | 1/1979 | Chora et al. | 502/208 |
| 4,179,358 | 12/1979 | Swift et al. | 502/64 |
| 4,385,994 | 5/1983 | Wilson et al. | 210/689 |

Primary Examiner—Delbert E. Gantz
Assistant Examiner—A. Pal
Attorney, Agent, or Firm—Gary L. Wamer

[57] ABSTRACT

By-product effluent streams from pyrolytic hydrocarbon cracking processes, containing monoolefins and diolefins, are treated to hydrogenate the olefins and to aromatize the aliphatics, with a catalyst comprising silicoaluminophosphates (SAPO-5, SAPO-11 etc.).

15 Claims, 2 Drawing Figures

CONVERSION OF CERTAIN HYDROCARBONS USING SILICOALUMINOPHOSPHATE CATALYSTS

BACKGROUND OF THE INVENTION

1. Field of the Invention

This invention relates to the preparation of streams containing recoverable benzene, toluene, and xylenes ("BTX") from initial by-product effluent streams that contain other components, notably monoolefins and diolefins. In one aspect, the invention concerns the removal by conversion of these other components which ordinarily prevent recovery by distillation or solvent extraction of benzene-toluene-xylenes aromatics from the streams. In another aspect, it concerns a low severity process for treating the by-product streams with a specified catalyst, and under defined reaction conditions, both to produce benzene-toluene-xylenes from the initial stream and to reduce or eliminate those components that otherwise would interfere with the economic recovery of these aromatics from the streams.

2. Description of the Prior Art

The preparation of light olefins and diolefins, mainly ethylene, propylene, and butadiene, by the thermal pyrolysis, or cracking, of petroleum fractions is well know and widely practiced. (See for example, Kirk & Othmer's "Encyclopedia of Chemical Technology", Second Edition, Vol. 8, pp. 503-514.) In these pyrolitic cracking processes, hydrocarbons ranging from ethane, through LPG (liquefied petroleum gas, chiefly propane with a few percent butanes), naphtha, heavy gas oil, to even crude petroleum oil, are subjected to high temperature conditions, at low pressure and for a short time, to produce a maximum of the desired product. These thermal processes vary widely, and the yields from any one process depend not only on process equipment and conditions, but on such extraneous factors as the presence or absence of diluents and other reactants, e.g., oxygen, hydrogen, steam, etc.

Even the best of the pyrolitic processes is less than ideally selective. As a consequence, the total reactor effluent will contain not only the desired olefin or diolefin, but a variety of other components, ranging from methane gas to high boiling polycyclic hydrocarbons. These by-products are conventionally separated, usually by distillation and/or absorption, so as to concentrate the main desired products for ultimate recovery, and to produce one or more by-product effluent streams.

The by-product effluents contain a mixture of hydrocarbon types, including paraffins, monoolefins, diolefins, aromatics, cyclics, and various substituted and polynuclear aromatics. Unless the by-product effluent stream or streams contains a particularly valuable or desirable component, making removal economical, the by-product effluent streams are of only limited utility. The lighter gases are useful only as fuel, while the heavier, normally liquid, components usually termed "dripolene," if not hydrogenated and then subjected to BTX extractions, are customarily either burned locally as fuel or else hydrogenated to saturate the unstable diolefins, and then blended with other gasoline factions as motor fuel.

It has long been recognized that some of these by-product effluent streams, particularly the dripolene factions, contain potentially valuable benzene, toluene, and xylenes (including ethylbenzene). Unfortunately, they also contain diolefins and monoolefins, which effectively interfere with most existing solvent extraction processes, such as the Udex and Sulfolane processes, for the extraction of aromatics from paraffins. Some of these olefins have boiling points similar to those of the BTX aromatics, and hence cannot be removed by fractional distillation. Selective hydrogenation to saturate the olefins and diolefins is practiced, and widely so, but the process tends to be expensive. Moreover, the diolefins in dripolene tend to be thermally unstable, forming catalyst-deactivating and exchanger-fouling carbonaceous deposits.

A variety of catalysts has been proposed for treating one or more of the by-product effluents from pyrolitic cracking processes so as to render the streams more valuable or more amenable to subsequent processing. (A tabulation of representative references identifying many of these processes, and many catalysts having conceivable useful activity for these processes, is appended.)

It is an object of the present invention to provide a process for preparing a stream from which benzene-toluene-xylenes may be recovered, by catalytically treating by-product effluent streams from pyrolytic hydrocarbon cracking processes. A further object is to provide a process for treating such by-product effluent stream in a simplified, low severity, operation so as both to produce benzene-toluene-xylenes (BTX), and, simultaneously, to decrease the content of interfering components. STill another object is to remove those monoolefins and diolefins which have heretofore interfered with the solvent extraction of BTX from dripolene and the like.

SUMMARY OF THE INVENTION

Briefly, in accordance with the invention, a stream from which benzene, toluene, and xylenes may be recovered readily is prepared by contacting a pyrolitic hydrocarbon cracking by-product effluent stream, containing substantial amounts of interfering monoolefins and diolefins, with a silicoaluminophosphate molecular sieve catalyst under low severity hydrocarbon processing conditions. As a result of this treatment, not only are some olefins hydrogenated to non-interfering aliphatics, but a substantial fraction of the aliphatics is dehydrocyclized to benzene-toluene-xylenes.

One of the remarkable aspects of the invention is that the low severity conditions of temperature, pressure, and space velocity, which are suitable for the hydrogenation, cyclization and dehydrogenation involved in the aromatization using the silicoaluminophosphate catalysts.

Thus, a simple processing scheme, with only a single reactor stage, is often adequate both to reduce to a minimal content, or eliminate the olefinic constituents that would interfere with the economic recovery of aromatics, and to produce benzene-toluene-xylenes from the feed stream.

A further important advantage of the invention resides in its ability to process any of a variety of the by-product effluent streams from pyrolitic cracking processes. As set out more fully below, these by-product effluent streams customarily include a $C_4$ fraction composed predominantly of butanes, butenes, and butadiene; a $C_5$ fraction composed mainly of pentanes, pentenes, pentadienes and cyclic $C_5$ compounds; a $C_6$–$C_8$ "dripolene" fraction containing BTX aromatics together with interfering olefins (i.e., having a similar boiling range); and a $C_9$-plus fraction, including some BTX along with higher alkylated benzenes and polynuclear aromatics and aliphatics. Each of these streams, plus others that may be present in a particular plant may be processed according to the invention.

The calcined silicoaluminophosphate catalysts for use with the present invention, to be identified more fully below, include those described U.S. Pat. No. 4,440,871, issued Apr. 3, 1984, incorporated herein by reference thereto.

Various other aspects of the invention are set out below.

DETAILED DESCRIPTION OF THE INVENTION

Pyrolitic Cracking Processes

Pyrolitic cracking processes for the preparation of light olefins and diolefins such as ethylene, propylene, and/or butadiene, have been described in the literature, and accordingly no detailed exposition is called for here.

In essense, the thermal pyrolysis, or cracking, of petroleum fractions may utilize as feed stocks hydrocarbons such as ethane, LPG (liquefied petroleum gas, chiefly propane with a few percent butanes), naphtha, heavy gas oil, or crude petroleum oil. These are subjected to controlled high temperature, low pressure, short time, pyrolitic cracking to produce the desired product or products. Thereafter the reactor effluent is subjected to a combination of condensation, fractional distillation, absorption, and perhaps other unit operations, to segregate various effluent streams enriched in one or more desirable components. The precise arrangement of product recovery streams forms no part of the present invention, and indeed it is probable that no two pyrolitic cracking plants utilize the same recovery scheme.

For example, the reactor effluent liquid may be subjected to fractional distillation to separate one or more fractions rich in benzene (B.P. 80.103° C.), toluene (B.P. 110.623° C.), and/or the xylenes, namely ethylbenzene (B.P. 136.187° C.), p-xylene (B.P. 138.348° C.), m-xylene (B.P. 139.102° C.), and o-xylene (B.P. 144.414° C.). This fraction, or fractions is desirably solvent extracted, as for example by the Udex or Solfolane process, to recover the BTX aromatic/aromatics.

In the absence of prior treatment, such as by the process of the present invention, solvent extraction is ineffective to extract the aromatics from the remaining aliphatics, inasmuch as solvents selective for aromatics will also extract many olefins and diolefins. However, the diolefins and the aromatics cannot be separated by fractional distillation; for example, benzene, with a boiling point of 80.103° C., is not easily distilled from the 2,4-hexadienes, which boil at about 80.0° C. Similarly, the various dimethylpentenes boil within a range of 72.2° C. to 85.0° C.

Be that as it may, and howsoever produced or constituted, there inevitably will be one or more by-product effluent streams which contain diverse mixtures of hydrocarbon (and perhaps non-hydrocarbon) components, varying both with respect to boiling point and chemical classification. It is this diversity that either complicates or prevents the recovery of useable components.

By way of example in an illustrative pyrolitic cracking plant, the total reactor effluent may be segregated into a predominantly gaseous fraction including recoverable ethylene and propylene; a crude $C_4$ fraction, a distillation cut which includes hydrocarbons with primarily four carbon atoms each; a crude $C_5$ fraction, another distillation cut which primarily contains hydrocarbon molecules with five carbon atoms each, and generally containing a large quantity of unsaturated and cyclic compounds, including olefins and lesser amounts of $C_4$'s and lighter $C_6$'s and heavier, a $C_6$–$C_8$ fraction, sometimes referred to as pyrolysis gasoline or dripolene; and a $C_9$ plus fraction, a heavier distillation cut which primarily includes hydrocarbons with at least nine carbon atoms, along with lesser amounts of $C_5$–$C_8$ hydrocarbons. The $C_9$ fraction generally is produced as the distillation bottoms from the processing of dripolene to remove pyrolysis gasoline, and contains components as widely varying as styrene, ethyltoluenes, and trimethylbenzenes, to heavier compounds including ethylnaphthalene, diphenyl, and dimethylnaphthalene.

An illustrative $C_4$ fraction, giving both the range and a typical composition, is set out in Table I below:

TABLE I

| | Illustrative $C_4$'s Composition | |
|---|---|---|
| Compound | Observed Range | Typical Composition |
| Lights | 0.4–5.0 wt % | 1.1 |
| Methylacetylene, Propadiene | 0.1–1.0 | 0.7 |
| n & i-Butane | 2.4–15.0 | 3.8 |
| 1-Butene and Isobutylene | 20.0–39.0 | 33.8 |
| t-2-Butene | 4.0–7.0 | 5.7 |
| c-2-Butene | 3.0–5.0 | 4.5 |
| 1,3-Butadiene | 41.0–54.0 | 44.6 |
| Vinylacetylene | 0.4–1.5 | 0.7 |
| Ethylacetylene | 0.1–0.5 | 0.2 |
| $C_{5+}$ | 0.2–5.0 | 4.1 |

Illustrative $C_5$ compositions, from two different plants, "A" and "B", are likewise represented in Table II, below:

TABLE II

| | Illustrative $C_5$'s Composition | | | |
|---|---|---|---|---|
| | Plant A | | Plant B | |
| Compound | Observed Range | Typical Composition | Observed Range | Typical Composition |
| $C_4$ and Lighter | 0–1.5 wt % | 0.7 | 1.4–8.1 | 5.5 |
| n & i Pentanes | 0–14.4 | 7.2 | 17.3–44.6 | 23.6 |
| $C_5$ Olefins | 0.1–11.3 | 4.6 | 6.6–37.4 | 9.9 |
| Pentadienes | 9.7–35.3 | 20.0 | 3.5–12.9 | 4.2 |
| Isoprene | 2.4–43.0 | 13.1 | 5.0–16.8 | 5.9 |
| Cyclopentane | 1.6–7.5 | 3.2 | 0–2.0 | — |
| Cyclopentene | 2.2–10.3 | 5.4 | 2.0–14.4 | 2.3 |
| Cyclopentadiene | 0.60–2.8 | 1.4 | 1.0–20.6 | 4.6 |
| $C_6$ Paraffins | 1.1–7.2 | 4.2 | 1.3–10.5 | 10.1 |
| $C_6$ Olefins | — | — | 0–3.0 | 0.2 |
| Benzene | 0.4–5.1 | 1.3 | 0.23.8 | 23.8 |

TABLE II-continued

| | Illustrative C$_5$'s Composition | | | |
|---|---|---|---|---|
| | Plant A | | Plant B | |
| Compound | Observed Range | Typical Composition | Observed Range | Typical Composition |
| Dicyclopentadiene | 19.3–48.1 | 32.1 | 1.0–21.0 | 1.8 |
| Other C$_{6+}$ | 1.5–14.8 | 6.8 | 0–9.0 | 8.1 |

Illustrative C$_9$ compositions, again from Plant "A" and Plant "B" are described in Table III below:

TABLE III

| | Illustrative C$_9$'s Composition | | | |
|---|---|---|---|---|
| | Plant A | | Plant B | |
| Compound | Observed Range | Typical Composition | Observed Range | Typical Composition |
| C$_5$–C$_8$ Nonaromatics | 0.5–4.4 | 0.5 | 0.2–3.4 | 0.2 |
| BTX | 0–9.8 | 1.7 | 0–31.9 | 1.2 |
| Styrene | 0.3–10.0 | 1.8 | 0–16.8 | 5.0 |
| Dicyclopentadiene | 7.2–40.0 | 29.2 | 4.7–42.0 | 40.5 |
| Methyl dicyclopentadiene and Dimethyldicyclopentadiene | 4.4–21.2 | 4.4 | 0–6.5 | 1.6 |
| Methyl Styrenes | 2.3–19.0 | 6.8 | 0–15.0 | 3.6 |
| C$_3$ Benzenes* | 8.0–26.0 | 12.7 | 0–12.5 | 7.3 |
| Indane | 0.2–16.9 | 13.8 | 0–6.9 | 0.2 |
| Indene | 3.9–15.6 | 9.9 | 1.0–13.0 | 9.8 |
| Naphthalenes | 0.6–9.3 | 3.5 | 3.0–15.0 | 14.1 |
| Other C$_{10+}$ | 10.7–32.6 | 15.7 | 14.6–48.6 | 16.7 |

*propyl benzenes, ethyl toluenes and trimethylbenzenes.

It will be appreciated, as noted earlier, that these compositions may vary quite widely, depending upon the initial feed to the pyrolitic cracking unit, the type of pyrolitic cracking unit, conditions in the pyrolitic unit, and the type and conditions of the product recovery section. The by-product effluent streams may likewise be blended with each other where this is desired, or may include recycle components from elsewhere in the product recovery section.

SILICOALUMINOPHOSPHATE COMPOSITIONS (SAPOs)

"Silicoaluminophosphate molecular sieves" (SAPOs) suitable as defined herein for use in the instant process comprise any molecular sieve having a silicoaluminophosphate molecular framework which comprises a molecular framework of corner-sharing [SiO$_2$] tetrahedra, [AlO$_2$] tetrahedra and [PO$_2$] tetrahedra, (i.e., (Si$_x$Al$_y$P)O$_2$ tetrahedral units), and which functions to convert at effective process conditions the aforementioned feedstock to products and includes those silicoaluminophosphate molecular sieves described U.S. Pat. No. 4,440,871.

The silicoaluminophosphate molecular sieves described U.S. Pat. No. 4,440,871, issued Apr. 3, 1984, incorporated herein by reference thereto, will be referred to hereinafter, solely for point of reference herein, as "SAPO" molecular sieves, or as "SAPOs" if the reference is to the class as a whole as employed herein. This designation is simply made for the sake of convenient reference herein and is not meant to designate a particular structure for any given silicoaluminophosphate (SAPO) molecular sieve. This class of SAPO's described is particularly well suited for use in the present process. The members of the class of SAPO's employed hereinafter in the examples will be characterized simply by referring to such members as SAPO-5, SAPO-11, etc., i.e., a particular species will be referred to as SAPO-n where "n" is a number specific to a given class member as its preparation is reported herein. This designation is an arbitrary one and is not intended to denote structure or relationship to another material(s) which may also be characterized by a numbering system.

Figure 1:
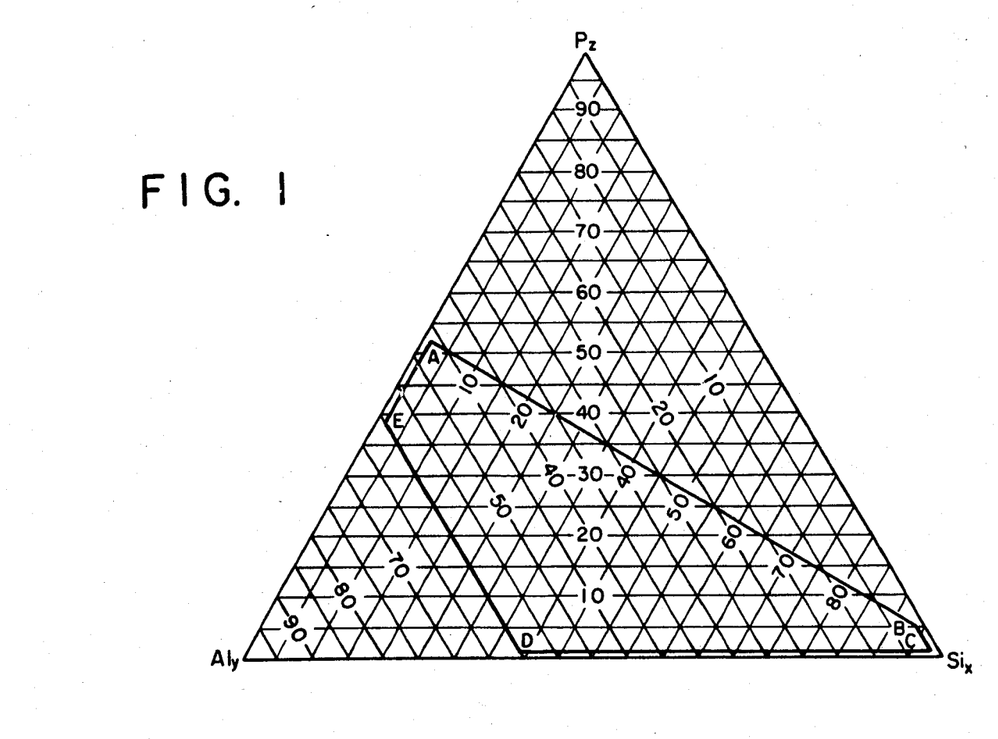
FIG. 1 is a ternary diagram showing the compositional parameters of the silicoaluminophosphates of U.S. Pat. No. 4,440,871 in terms of mole fractions of silicon, aluminum and phorphorus.

The preferred SAPO's are characterized as comprising a three-dimensional microporous crystal framework structure of [SiO$_2$], [AlO$_2$] and [PO$_2$] tetrahedral units which has a unit empirical formula on an anhydrous basis of:

$$mR: (Si_xAl_yP_z)O_2 \qquad (1)$$

wherein "R" represents at least one organic templating agent (hereinafter also referred to as "template") present in the intracrystalline pore system; "m" represents the moles of "R" present per mole of (Si$_x$Al$_y$P$_z$)O$_2$ and has a value from zero (0) to about 0.3, with the maximum value of m being related, at least in part, to the molecular dimensions of the template and the void volume of the intracrystalline pore system of the particular SAPO; "x", "y" and "z" represent the mole fractions of silicon, aluminum and phosphorus, respectively, present as tetrahedral oxide units, said mole fractions being within the pentagonal compositional area defined by points A, B, C, D and E of the ternary compositional diagram depicted by FIG. 1 of the drawings where the points A, B, C, D and E are represented by the following values for "x", "y" and "z":

| | Mole Fraction | | |
|---|---|---|---|
| Point | x | y | z |
| A | 0.01 | 0.47 | 0.52 |
| B | 0.94 | 0.01 | 0.05 |
| C | 0.98 | 0.01 | 0.01 |
| D | 0.39 | 0.60 | 0.01 |
| E | 0.01 | 0.60 | 0.39 |

Figure 2:
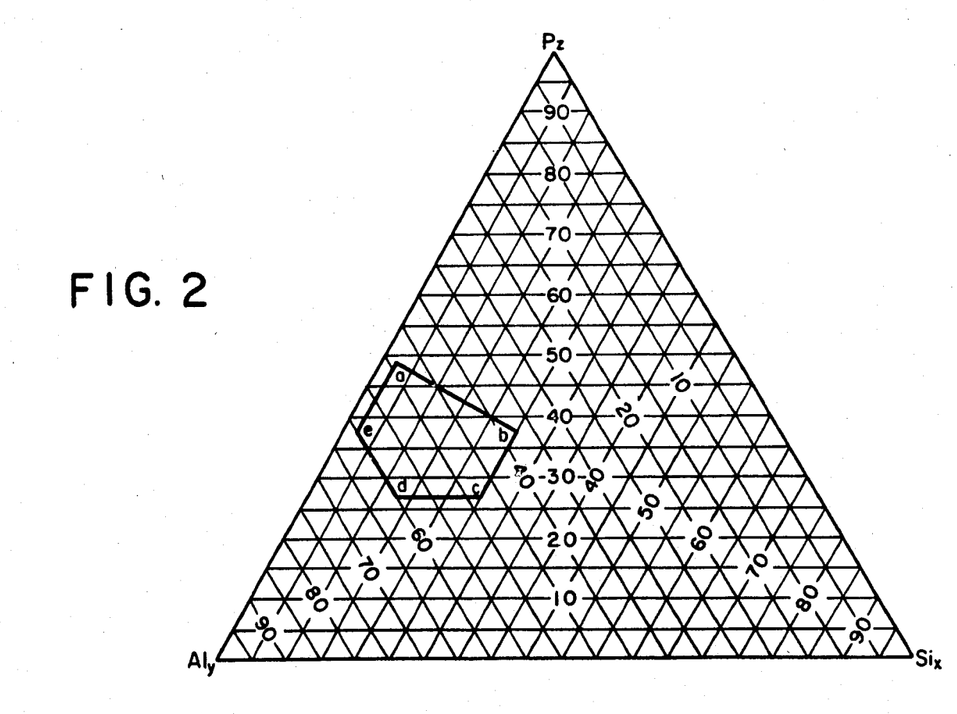
FIG. 2 is a ternary diagram showing the preferred compositional parameters of the silicoaluminophosphates of mole fractions of silicon, aluminum and phsophorus.

A preferred sub-class of the SAPOs of Formula (1), above, have a minimum value for "m" of 0.02 in the as-synthesized form and have values for "x", "y" and "z" within the pentagonal compositional area defined by the points a, b, c, d and e of the ternary diagram which is FIG. 2 of the drawings, wherein said points a, b, c, d and e are represented by the following values for "x", "y" and "z":

| | Mole Fraction | | |
|---|---|---|---|
| Point | x | y | z |
| a | 0.02 | 0.49 | 0.49 |
| b | 0.25 | 0.37 | 0.38 |
| c | 0.25 | 0.48 | 0.27 |
| d | 0.13 | 0.60 | 0.27 |
| e | 0.02 | 0.60 | 0.38 |

The term "unit empirical formula" is used herein according to its common meaning to designate the simplest formula which gives the relative number of atoms of silicon, aluminum and phosphorus which form a [PO$_2$], [AlO$_2$] and [SiO$_2$] tetrahedral unit within a silicoaluminophosphate molecular sieve and which forms the molecular framework of the SAPO composition(s). The unit empirical formula is given in terms of silicon, aluminum and phosphorus as shown in Formula

(1), above, and does not include other compounds, cations or anions which may be present as a result of the SAPO's preparation or the existence of other impurities or materials in the bulk composition not containing the aforementioned tetrahedral unit as the molecular framework. The amount of template R is reported as part of the composition when the as-synthesized unit empirical formula is given, and water may also be reported unless such is defined as the anhydrous form. For convenience, coefficient "m" for template "R" is reported as a value that is normalized by dividing the number of moles of R by the total number of moles of silicon, phosphorus and aluminum. When moles of water are reported the mores of water relative to the mole fractions of silicon, aluminum and phosphorus is reported as a value that is normalized by dividing the number of moles of water by the total moles of silicon, phosphorus and aluminum. The values for x, y and z are determined by dividing the number of moles of silicon, aluminum, and phosphorus individually by the total number of moles of silicon, aluminum and phosphorus.

The unit empirical formula for a SAPO may be given on an "as-synthesized" basis or may be given after an "as-synthesized" SAPO composition has been subjected to some post treatment process, e.g., calcined. The term "as-synthesized" herein shall be used to refer to the SAPO composition(s) formed as a result of the hydrothermal crystallization but before the SAPO composition has been subjected to post treatment to remove any volatile components present therein. The actual value of "m" for a post-treated SAPO will depend on several factors (including: the particular SAPO, template, severity of the post-treatment in terms of its ability to remove the template from the SAPO, the proposed application of the SAPO composition, and etc.) and the value for "m" can be within the range of values as defined for the as-synthesized SAPO compositions although such is generally less than the as-synthesized SAPO unless such post-treatment process adds template to the SAPO so treated. A SAPO composition which is in the calcined or other post-treated form generally has an empirical formula represented by Formula (1), except that the value of "m" is generally less than about 0.02. Under sufficiently severe post-treatment conditions, e.g. roasting in air at high temperature for long periods (over 1 hr.), the value of "m" may be zero (0) or, in any event, the template, R, is undetectable by normal analytical procedures.

The above silicoaluminophosphates are generally synthesized by hydrothermal crystallization from a reaction mixture comprising reactive sources of silicon, aluminum and phosphorus, and one or more organic templating agents. Optionally, alkali metal(s) may be present in the reaction mixture. The reaction mixture is placed in a sealed pressure vessel, preferably lined with an inert plastic material, such as polytetrafluoroethylene, and heated, preferably under autogenous pressure at a temperature of at least about 100° C., and preferably between 100° C. and 250° C., until crystals of the silicoaluminophosphate product are obtained, usually for a period of from 2 hours to 2 weeks. While not essential to the synthesis of SAPO compositions, it has been found that in general stirring or other moderate agitation of the reaction mixture and/or seeding the reaction mixture with seed crystals of either the SAPO to be produced, or a topologically similar composition, facilitates the crystallization procedure. The product is recovered by any convenient method such as centrifugation or filtration.

After crystallization the SAPO may be isolated and washed with water and dried in air. As a result of the hydrothermal crystallization, the as-synthesized SAPO contains within its intracrystalline pore system at least one form of the template employed in its formation. Generally, the template is a molecular species, but it is possible, steric considerations permitting, that at least some of the template is present as a charge-balancing cation. Generally the template is too large to move freely through the intracrystalline pore system of the formed SAPO and may be removed by a post-treatment process, such as by calcining the SAPO at temperatures of between about 200° C. and to about 700° C. so as to thermally degrade the template or by employing some other post-treatment process for removal of at least part of the template from the SAPO. In some instances the pores of the SAPO are sufficiently large to permit transport of the template, and, accordingly, complete or partial removal thereof can be accomplished by conventional desorption procedures such as carried out in the case of zeolites.

The SAPOs are preferably formed from a reaction mixture having a mole fraction of alkali metal cation which is sufficiently low that it does not interfere with the formation of the SAPO composition. Although the SAPO compositions will form if alkali metal cation are present, such reaction mixtures are not generally preferred. A reaction mixture, expressed in terms of molar oxide ratios, having the following bulk composition is preferred:

$$aR_2O:(Si_xAl_yP_z)O_2:bH_2O$$

wherein "R" is a template; "a" has a value great enough to constitute an effective concentration of "R" and is within the range of from greater than zero (0) to about 3; "b" has a value of from zero to 500; "x", "y" and "z" represent the mole fractions, respectively of silicon, aluminum and phosphorus wherein x, y and z each have a value of at least 0.01. The reaction mixture is preferably formed by combining at least a portion of the reactive aluminum and phosphorus sources in the substantial absence of the silicon source and thereafter combining the resulting reaction mixture comprising the aluminum and phosphorus sources with the silicon source. When the SAPOs are synthesized by this method the value of "m" in Formula (1) is generally above about 0.02.

Though the presence of alkali metal cations are not preferred, when they are present in the reaction mixture it is preferred to first admix at least a portion of each of the aluminum and phosphorus sources in the substantial absence of the silicon source. This procedure avoids adding the phosphorus source to a highly basic reaction mixture containing the silicon and aluminum source, (as was done in most of the published attempts to substitute isomorphously [PO_2] tetrahedra for [SiO_2] tetrahedra in zeolite structures). Although the reaction mechanism is by no means clear at this time, the function of the template may be to favor the incorporation of [PO_2] and [AlO_2] tetrahedra in the framework structures of the crystalline products with [SiO_2] tetrahedra isomorphously replacing [PO_2] tetrahedra.

The reaction mixture from which these SAPOs are formed contain one or more organic templating agents (templates) which can be most any of those heretofore proposed for use in the synthesis of aluminosilicates and aluminophosphates. The template preferably contains at least one element of Group VA of the Periodic Table, particularly nitrogen, phosphorus, arsenic and/or antimony, more preferably nitrogen or phosphorus and most preferably nitrogen. The template contains at least one alkyl, aryl, araalkyl, or alkylaryl group. The template preferably contains from 1 to 8 carbon atoms, although more than eight carbon atoms may be present in the template. Nitrogen-containing templates are preferred, including amines and quaternary ammonium compounds, the latter being represented generally by the formula $R'_4N^+$ wherein each $R'$ is an alkyl, aryl, alkylaryl, or araalkyl group; wherein $R'$ preferably contains from 1 to 8 carbon atoms or higher when $R'$ is alkyl and greater than 6 carbon atoms when $R'$ is otherwise, as hereinbefore discussed. Polymeric quaternary ammonium salts such as $[(C_{14}H_{32}N_2)(OH)_2]_x$ wherein "x" has a value of at least 2 may also be employed. The mono-, di- and, tri-amines, including mixed amines, may also be employed as templates either alone or in combination with a quaternary ammonium compound or another template. The exact relationship of various templates when concurrently employed is not clearly understood. Mixtures of two or more templating agents can produce either mixtures of SAPOs or in the instance where one template is more strongly directing than another template the more strongly directing template may control the course of the hydrothermal crystallization wherein with the other template serving primarily to establish the pH conditions of the reaction mixture.

Representative templates include tetramethylammonium, tetraethylammonium, tetrapropylammonium or tetrabutylammonium ions; di-n-propylamine; tripropylamine; triethylamine; triethanolamine; piperidine; cyclohexylamine; 2-methylpyridine; N,N-dimethylbenzylamine; N,N-diethylethanolamine; dicyclohexylamine; N,N-dimethylethanolamine; choline; N,N'-dimethylpiperazine; 1,4-diazabicyclo (2,2,2) octane; N-methyldiethanolamine, N-methylethanolamine; N-methylpiperidine; 3-methylpiperidine; N-methylcyclohexylamine; 3-methylpyridine; 4-methylpyridine; quinuclidine; N,N'-dimethyl-1,4-diazabicyclo (2,2,2) octane ion; di-n-butylamine, neopentylamine; di-n-pentylamine; isopropylamine; t-butylamine; ethylenediamine; pyrrolidine; and 2-imidazolidone. As will be readily apparent from the illustrative examples set forth hereinafter, not every template will produce every SAPO composition although a single template can, with proper selection of the reaction conditions, cause the formation of different SAPO compositions, and a given SAPO composition can be produced using different templates.

In those instances where an aluminum alkoxide is the reactive aluminum source, the corresponding alcohol is necessarily present in the reaction mixture since it is a hydrolysis product of the alkoxide. It has not as yet been determined whether this alcohol participates in the synthesis process as a templating agent, or in some other function and, accordingly, is not reported as a template in the unit formula of the SAPOs, although such may be acting as templates.

Alkali metal cations in the reaction mixture may facilitate the crystallization of certain SAPO phases, although the exact function of such cations in crystallization, if any, is not presently known. Alkali cations present in the reaction mixture generally appear in the formed SAPO composition, either as occluded (extraneous) cations and/or as structure cations balancing net negative charges at various sites in the crystal lattice. It should be understood that although the unit formula for the SAPOs does not specifically recite the presence of alkali cations they are not excluded in the same sense that hydrogen cations and/or hydroxyl groups are not specifically provided for in the traditional formulae for zeolitic aluminosilicates.

Most any reactive phosphorus source may be employed herein such that $[PO_2]$ tetrahedra are provided for in the SAPO framework. Phosphoric acid is the most suitable phosphorus source employed to date. Accordingly, other acids of phosphorus are generally believed to be suitable phosphorus sources for use herein. Organic phosphates such as triethyl phosphate have been found satisfactory, and so also have crystalline or amorphous aluminophospates such as the $AlPO_4$ compositions of U.S. Pat. No. 4,310,440. Organo-phosphorus compounds, such as tetrabutylphosphonium bromide have not, apparently, served as reactive sources of phosphorus, but these compounds do function as templating agents and may also be capable of being suitable phosphorus sources under proper process conditions (yet to be ascertained). Organic phosphorus compounds, e.g. esters, are believed to be generally suitable since they can generate acids of phosphorus in situ. Conventional phosphorus salts, such as sodium metaphosphate, may be used, at least in part as the phosphorus source, but they are not preferred.

Most any reactive aluminum source may be employed herein such that $[AlO_2]$ tetrahedra are provided for incorporation in the SAPO framework. The preferred reactive aluminum sources include aluminum alkoxides, such as aluminum isoproproxide, and pseudo-boehmite. Crystalline or amorphous aluminophosphates which are a suitable source of phosphorus are, of course, also suitable sources of aluminum. Other sources of aluminum used in zeolite synthesis, such as gibbsite, sodium aluminate and aluminum trichloride, can be employed but are generally not preferred.

Most any reactive silicon source may be employed herein such that $[SiO_2]$ tetrahedra are provided for incorporation in the SAPO framework. Silicon is preferably introduced into the reaction system as either a silica sol or as fumed silica, but other conventional sources of silicon used in zeolite synthesis procedures can be employed. For example, a reactive solid amorphous precipitated silica, silica gel, silicic acid or alkali metal silicate may be employed as the silicon source with the last two named not being preferred. The silicon source material is preferably not an alkali metal silicate owing to the high pH conditions necessarily imparted to reaction mixtures by such alkali metal silicates where high molar $SiO_2/Al_2O_3$ ratios are desired, since such result in a marked tendency to produce extraneous aluminophosphates compositions. While the high pH conditions can be avoided by in situ neutralization with an acid and the consequent formation of a precipitated silica, this is, in effect, the use of silica as the reactive silicon source rather than an alkali metal silicate. Accordingly, if alkali metal silicate is employed as a reagent, it is preferably used in conjunction with another source of reactive silicon and the alkali metal silicate comprises a minor proportion (less than 50 percent by weight) of the overall reactive silicon source with the reaction mixture having the same composition, expressed in terms of mole ratios of oxides, as set forth hereinabove for the process wherein such alkali metals are present in the reaction mixture.

When used in the present process, the silicoaluminophosphates may be employed either alone or in intimate admixture with independently active catalytic components, as for example the noble metals such as platinum, or other catalytically active metals such as molybdenum, vanadium, zinc, etc. The techniques of introducing catalytically active metals to a molecular sieve are disclosed in the literature, and preexisting metal incorporation techniques are suitable. See, for example, Rabo et al. U.S. Pat. Nos. 3,236,761 and 3,236,762.

The physical form of the silicoaluminophosphate catalyst depends on the type of catalytic reactor being employed and may be in the form of a granule or powder, and is desirably compacted into a more readily usable form (e.g., larger agglomerates), usually with a silica or alumina binder for fluidized bed reaction, or pills, prills, spheres, extrudates, or other shapes of controlled size to accord adequate catalyst-reactant contact. As indicated, the catalyst may be employed either as a fluidized catalyst, or in a fixed or moving bed, and in one or more reaction stages.

Conversion Parameters

The conversion parameters, while broad, may be selected to provide a high degree of versatility, depending upon the feed composition and on the desired product quality.

With respect to temperature, a temperature within the range of about 300°–700° C., more preferably within the range of about 350°–600° C., is adequate for many, if not all, conversions. Higher temperatures give more rapid and more complete reaction, but tend to produce undesirable by-products, chiefly coke, and may otherwise disturb the optimum balance of product composition with on-stream ease of operation.

The pressure, almost uniquely, is desirably quite low. Atmospheric pressure operation has been used successfully in the laboratory, but under specific conditions may be as high as 100 atmospheres or more. A desirable range is from atmospheric pressure to about 7 atmospheres. High pressures facilitate hydrogenation; lower pressures facilitate dehydrocyclization. The optimum pressure will therefore depend on process economics, considering whether it is more desirable to hydrogenate olefins than to produce a high yield of BTX aromatics.

Process stream flow rate, as expressed in units of weight hourly space velocity (WHSV), or weight of hydrocarbon feed per unit weight of catalyst, is suitably within the range of about 0.1 to about 20, more desirably about 0.5–5.0. High WHSV's permit more economic plant construction, while lower WHSV's permit more complete reaction at given temperature-pressure conditions.

If desired, a gaseous or gasifiable diluent may be introduced along with the hydrocarbon feed to the silicoaluminophosphate catalyst. This diluent may be inert, typified by steam, nitrogen or a low boiling paraffin and mixtures thereof, or may be reactive with the feed under analysis conditions (e.g., hydrogen). Hydrogen is particularly desirable as it minimizes coke formation and deposition on the catalyst, with resulting premature deactivation, and also facilitates hydrogenation, as demonstrated below, however, the techniques of the present invention need not utilize hydrogen.

If either an inert or a reactive gas is employed, diluent/hydrocarbon molar (gas volume) ratios, optimally, of from 0.1 to about 10 may be employed.

It is usually necessary that the catalyst be regenerated, either periodically or continuously, to remove the carbonaceous coke-like deposits from the catalyst. In a fluidized bed operation, a portion of the catalyst is continuously withdrawn from the reactor and then subjected to regeneration by combustion with air or other oxygen containing gas, after which it is continuously recycled to the reactor. In a moving bed operation, the removal of catalyst followed by regeneration may be effected either continuously or periodically. In a fixed bed operation, it is generally desirable that two or more reactors be used in parallel, so that when one is processing the hydrocarbon feed, the other is out of service and being regenerated. Regeneration conditions of approximately 450°–650° C., preferably 500°–600° C. may be employed.

EXPERIMENTAL PROCEDURE

Examples 1 to 10 were carried out using a hydrocarbon effluent from a thermal pyrolysis unit comprising a crude butadiene hydrocarbon effluent having the following analysis:

| CRUDE BUTADIENE COMPOSITION | |
|---|---|
| | Weight Percent |
| $C_3$ and lighter | 1.24 |
| Isobutane | 2.57 |
| n-Butane | 8.68 |
| 1-Butene and Isobutene | 33.74 |
| t-2-Butene | 4.15 |
| c-2-Butene | 2.44 |
| 1,3 Butadiene | 45.72 |
| $C_4$ Acetylenes | 1.28 |
| $C_{5+}$ Hydrocarbons | 0.19 |

Examples 1 to 10 were carried out using a modified Chromalytics Model MP-3 Thermal Chromatograph. The SAPO catalyst was activated in situ at a temperature of 550° C. for one hour prior to use in the examples. After activation 0.25 gram of the SAPO catalyst (in the form of a powder) was placed in the reaction chamber (6 mm O.D.) between two plugs of glass wool. The catalyst was then purged with helium. The temperature of the reaction chamber and SAPO catalyst was increased to 450° C. at which point the flow of helium was discontinued and the crude butadiene feed contacted with the SAPO catalyst at 5 cubic centimeters per minute (cc/min) for ten minutes. The products were collected in a liquid nitrogen trap (POROPAK Q-SE 30) and the products were collected for the same time frame for each SAPO catalyst after the butadiene feed had contacted the SAPO catalyst. The butadiene feed was then discontinued and a helium purge begun. The nitrogen trap was then backflushed and rapidly heated to 200° C. The desorbed products are analyzed by vapor phase chromatograph using either a 30 ft. or 40 ft. OV-101 column at a helium flow of 20 cc/min and at a column temperature program of 4° C./minute from ambient temperature to 200° C. The vapor phase chromatograph was equipped with a flame ionization detector and a thermal conductivity detector and the results compiled by a PDP-1134 minicomputer interfaced directly to the gas chromatograph. The results of examples 1–10 are reported as weight percent and were derived from the area percents. The weight percents are deemed to have an accuracy of ±5 percent.

Examples 11 to 18 were carried out using a 0.75 inch (OD) stainless steel tubular reactor. The reactor was equipped with thermocouples and electrical heaters for monitoring and controlling the temperature of the catalyst and feed. The examples were carried out by heating the reactor to reaction temperature from ambient temperature under a nitrogen purge. The feed was then introduced by standard metering, e.g., Brooks rotameter, and product samples collected, both vapor and liquid. The gas samples were analyzed on an HP 5730A chromatograph and the liquid samples analyzed on a Varian 4600 chromatograph and the products are reported as weight percents. The SAPO catalyst was either a fresh catalyst or was a regenerated catalyst. When a fresh catalyst was employed the catalyst was first activated by contacting it with air (450 cc/min) at a reactor temperature of about 550° C. When a regenerated catalyst was employed it was regenerated by contacting the catalyst with a 1:1 volume ratio of nitrogen to air and gradually increasing the amount of air used until substantially no nitrogen is present. The temperature of the catalyst was maintained above about 550° C. but less than about 620° C. during the regeneration. The regeneration is continued until the carbon dioxide content in the effluent from the regeneration is below about 0.5 percent by weight.

Examples 11–15 were carried out by employing a SAPO-11 catalyst which had been formed by mixing 25.29 grams of SAPO-11 with 5.06 grams of a gamma-alumina. The resulting mixture was extruded to form 0.25 inch×1/16 inch pellets. The pellets were then crushed and screened to give a catalyst having an average particle size of 0.5 cm×0.5 cm×0.25 cm. The catalyst was placed in the ¾ inch (OD) stainless steel reactor, as above described, in an amount of 31.4 grams, including adsorbed water, with about four inches of quartz chips being placed at the bottom of the reactor.

Examples 16 to 18 were carried out in a manner similar to examples 11–15 except that the SAPO-5 was employed and was formulated by mixing 26.08 grams of SAPO-5 with 5.24 grams of gamma-alumina. The reactor was charged with 32.8 grams of SAPO-5 catalyst for examples 16 to 18.

EXAMPLES 1 TO 5

In examples 1 to 5, SAPO-5, SAPO-11, SAPO-31, SAPO-34 and SAPO-45 were employed as catalysts at at temperature of 450° C., at ambient pressure and by introducing the crude butadiene at a rate of 5 cc/min. The products were analyzed by vapor phase chromatography and had the following analysis, as shown in Table IV:

TABLE IV

| Compounds | Example 1 (SAPO-11) | Example 2 (SAPO-31) | Example 3 (SAPO-5) | Example 4 (SAPO-34) | Example 5 (SAPO-45) |
|---|---|---|---|---|---|
| $C_1$–$C_4$ | 30.4 | 34.0 | 54.4 | 76.1 | 82.5 |
| $C_5$ + $C_6$ Aliphatics | 5.8 | 8.2 | 7.3 | 2.0 | 2.9 |
| Benzene | 2.5 | 1.9 | 1.3 | 0.2 | 0.7 |
| $C_7$ Aliphatics | 2.6 | 5.4 | 6.1 | 1.0 | 0.5 |
| Toluene | 3.6 | 3.8 | 4.6 | 0.1 | 0.8 |
| $C_8$ Aliphatics | 7.0 | 12.2 | 11.5 | 7.5 | 4.6 |
| Ethylbenzene, Xylenes | 14.2 | 10.5 | 2.4 | 8.4 | 3.2 |
| $C_{9+}$ Hydrocarbons | 33.8 | 24.0 | 12.4 | 4.7 | 4.9 |

EXAMPLE 6

SAPO-11 was evaluated as in examples 1 to 5, except that the crude butadiene feed was saturated with water at 50° C. prior to contacting it with SAPO-11. Analysis of the products gave the following:

| Compounds | Weight Percents |
|---|---|
| $C_1$–$C_4$ | 28.3 |
| $C_5$ + $C_6$ Aliphatics | 8.4 |
| Benzene | 1.2 |
| $C_7$ Aliphatics | 3.2 |
| Toluene | 3.0 |
| $C_8$ Aliphatics | 27.6 |
| Ethylbenzene, Xylenes | 14.2 |
| $C_{9+}$ Hydrocarbons | 14.1 |

EXAMPLES 7 & 8

SAPO-11 was evaluated as in examples 1 to 5 but at 400° C. (example 7) and at 500° C. (example 8). Analysis of the products in weight percents gave the following:

| Compounds | Example 7* T = 400° C. | Example 8* T = 500° C. |
|---|---|---|
| $C_1$–$C_4$ | 25.6 | 25.2 |
| $C_5$ + $C_6$ Aliphatics | 3.0 | 7.9 |
| Benzene | 0.4 | 2.2 |
| $C_7$ Aliphatics | 3.3 | 5.3 |
| Toluene | 1.5 | 2.9 |
| $C_8$ Aliphatics | 32.3 | 20.3 |
| Ethylbenzene, Xylenes | 15.2 | 17.7 |
| $C_{9+}$ Hydrocarbons | 18.7 | 18.5 |

*T = Temperature in °C.

EXAMPLE 9

SAPO-34 was evaluated as in examples 1 to 5 except that the crude butadiene feed was saturated with water prior to contacting it with SAPO-34. Analysis of the products gavew the following:

| Compounds | Weight Percents |
|---|---|
| $C_1$–$C_4$ | 64.95 |
| $C_5$ + $C_6$ Aliphatics | 3.54 |
| Benzene | —* |
| $C_7$ Aliphatics | 3.81 |
| Toluene | 0.36 |
| $C_8$ Aliphatics | 21.12 |
| Ethylbenzene, Xylenes | 2.28 |
| $C_{9+}$ Hydrocarbons | 3.92 |

*not detected

EXAMPLE 10

SAPO-11 was evaluated as in examples 1 to 5 and the products analyzed by a gas chromatograph-mass spectrometer. The following analysis was obtained.

| Compounds | Weight Percents |
|---|---|
| $C_1$–$C_3$ | 7.1 |
| Butane | 25.4 |

| Compounds | Weight Percents |
|---|---|
| -continued | |
| Butenes | 22.0 |
| $C_5 + C_6$ Aliphatics | 4.0 |
| Benzene | 1.3 |
| $C_7$ Aliphatics | 1.1 |
| Toluene | 2.4 |
| $C_8$ Aliphatics | 6.0 |
| Ethylbenzene, xylenes | 14.2 |
| $C_{9+}$ Hydrocarbons | 16.4 |

EXAMPLE 11

SAPO-11 was evaluated according to the above procedure at ambient pressure employing a crude butadiene feed having a composition substantially the same as the "Typical Composition" of Table I. The catalyst was activated prior to use. The crude butadiene feed was introduced to the reactor at the rate of 2.55 grams feed per gram of catalyst per hour. The average reactor temperature was 400° C. The analysis of the products at 6 hours gave the following:

| Component | 6 Hrs. |
|---|---|
| $C_1$-$C_3$ | 7.1 |
| Isobutane | 1.3 |
| n-Butane | 2.9 |
| 1-Butene and Isobutylene | 30.7 |
| t-2-Butene | 8.4 |
| c-2-Butene | 6.6 |
| 1,3-Butadiene | 11.5 |
| $C_5$ Hydrocarbons | 1.4 |
| $C_6$-$C_8$ Nonaromatics | 13.5 |
| Benzene | 0.3 |
| Toluene | 1.2 |
| Ethylbenzene and mixed xylenes | 6.9 |
| $C_{9+}$ Aromatics | 2.6 |
| Other $C_{9+}$ Hydrocarbons | 5.6 |

*weight percents

EXAMPLE 12

The SAPO-11 of example 11 was regenerated and employed as in example 11 except that the feed rate was 0.50 grams of feed per gram of catalyst per hour and the average reactor temperature was 190° C. Analysis of the products at one (1) and six (6) hours gave the following:

| Component | 1 Hr. | 6 Hrs. |
|---|---|---|
| $C_1$-$C_3$ | 32.9 | 20.2 |
| Isobutane | 5.7 | 3.1 |
| n-Butane | 5.8 | 4.4 |
| 1-Butene and Isobutylene | 16.5 | 30.8 |
| t-2-Butene | 7.1 | 11.0 |
| c-2-Butene | 4.7 | 7.3 |
| 1,3-Butadiene | 0.0 | 0.2 |
| $C_5$ Hydrocarbons | 5.5 | 3.5 |
| $C_6$-$C_8$ Nonaromatics | 2.5 | 2.6 |
| Benzene | 0.8 | 1.4 |
| Toluene | 3.0 | 2.6 |
| Ethylbenzene and mixed xylenes | 7.3 | 6.5 |
| $C_{9+}$ Aromatics | 5.7 | 4.7 |
| Other $C_{9+}$ Hydrocarbons | 2.5 | 1.9 |

EXAMPLES 13 AND 14

Examples 13 and 14 were carried out using a C-dripolene feed having the following analysis:

| C-DRIPOLENE FEED COMPOSITIONS | | |
|---|---|---|
| | Example 13 | Example 14 |
| $C_3$'s | 0 | 0.1 |
| $C_4$'s | 0.1 | 1.2 |
| $C_5$'s | 10.5 | 6.3 |
| $C_6$-$C_8$ Nonaromatics | 7.8 | 7.3 |
| Benzene | 24.7 | 40.0 |
| Toluene | 15.7 | 12.3 |
| Ethylenebenzene, Mixed Xylenes | 16.0 | 10.7 |
| $C_{9+}$ Aromatics | 11.3 | 8.9 |
| Other $C_{9+}$ Hydrocarbons | 14.0 | 13.2 |

Example 13 was carried out using the SAPO-11 catalyst of example 12 after regeneration. The procedure of example 11 was followed except that the feed rate was 1.24 g of feed per gram of catalyst per hour with an average reactor temperature of 482° C. Analysis of the products at 6 hours gave the following:

| Component | 6 Hrs. |
|---|---|
| $C_1$-$C_4$ | 8.1 |
| $C_5$ Hydrocarbons | 13.1 |
| $C_6$-$C_8$ Nonaromatics | 5.5 |
| Benzene | 26.7 |
| Toluene | 16.2 |
| Ethylbenzene and mixed xylenes | 16.8 |
| $C_{9+}$ Aromatics | 10.6 |
| Other $C_{9+}$ Hydrocarbons | 4.0 |

Example 14 was carried out using the catalyst of example 13 after regeneration. The procedure was the same as in example 13 except that the feed rate was 1.20 grams of feed per gram of catalyst per hour with the average reactor temperature being 483° C. Analysis of the products at 6 hours gave the following:

| Component | 6 Hrs. |
|---|---|
| $C_1$-$C_4$ | 5.1 |
| $C_5$ Hydrocarbons | 7.1 |
| $C_6$-$C_8$ Nonaromatics | 4.6 |
| Benzene | 43.2 |
| Toluene | 13.5 |
| Ethylbenzene and mixed xylenes | 11.4 |
| $C_{9+}$ Aromatics | 11.2 |
| Other $C_{9+}$ Hydrocarbons | 3.9 |

EXAMPLE 15

SAPO-11 was evaluated using a fractionated $C_{9+}$ by-product hydrocarbon feed having the following analysis.

| FRACTIONED $C_9$'s HYDROCARBON FEED | |
|---|---|
| Compound | Observed Range |
| $C_5$-$C_8$ Nonaromatics | 0.8 |
| BTX | 1.3 |
| Styrene | 0.4 |
| Dicyclopentadiene | 59.6 |
| Methyl dicyclopentadiene and Dimethyldicyclopentadiene | 10.8 |
| Methyl Styrenes | 0.7 |
| $C_3$ Benzenes* | 9.0 |
| Indane | 1.4 |
| Indene | 13.7 |
| Naphthalenes | 1.6 |

-continued

| FRACTIONED C₉'s HYDROCARBON FEED | |
|---|---|
| Compound | Observed Range |
| Other $C_{10}+$ | 0.8 |

*propyl benzenes, ethyl toluenes and trimethyl benzenes.

The procedure of example 11 was followed except the feed rate was 0.60 grams of feed per gram of catalyst per hour and hydrogen was employed as a diluent with 9.3 moles of hydrogen used per mole of feed. The average reactor temperature was 418° C. Analysis of the products at one (1) and six (6) hours gave the following:

| Component | 1 Hr. | 6 Hrs. |
|---|---|---|
| $C_1-C_4$ | 29.0 | 31.4 |
| $C_5$ Hydrocarbons | 4.0 | 10.7 |
| $C_6-C_8$ Nonaromatics | 2.1 | 1.9 |
| Benzene | 2.7 | 1.6 |
| Toluene | 3.8 | 0.9 |
| Ethylbenzene and mixed xylenes | 4.9 | 1.9 |
| $C_9+$ Aromatics | 31.9 | 26.3 |
| Other $C_9+$ Hydrocarbons | 21.4 | 25.3 |

EXAMPLE 16

SAPO-5 was evaluated using a crude butadiene feed having substantially the same composition as the "Typical Composition" of Table I. The procedure was the same as in example 11, except that the feed rate was 2.47 grams of feed per gram of catalyst per hour with an average reactor temperature of 411° C. Analysis of the products at 1 and 6 hours gave the following:

| Component | 1 Hr. | 6 Hrs. |
|---|---|---|
| $C_1-C_3$ | 6.5 | 6.0 |
| n-Butane | 2.8 | 2.7 |
| 1-Butene, Isobutylene, Butane | 35.4 | 37.0 |
| Methyl Acetylene | 0.3 | 0.6 |
| t-2-Butene | 6.9 | 5.3 |
| c-2 Butene | 4.9 | 3.6 |
| 1,3-Butadiene | 37.5 | 42.1 |
| $C_5$ Hydrocarbons | 0.3 | 0.3 |
| $C_6-C_8$ Nonaromatics | 2.2 | 1.5 |
| Benzene and Cyclohexane | 0.1 | 0.0 |
| Toluene | 0.1 | 0.0 |
| Ethybenzene and Mixed Xylenes | 1.3 | 0.3 |
| $C_9+$ Armomatics | 0.5 | 0.1 |
| Other $C_9+$ Hydrocarbons | 1.1 | 0.3 |

EXAMPLE 17

SAPO-5 was evaluated using the C-dripolene feed of example 14 according to the procedure of example 11, except the feed rate was 1.03 grams of feed per gram of catalyst per hour with an average reactor temperature of 496° C. Analysis of the products at 6 hours gave the following:

| Component | 6 Hrs. |
|---|---|
| $C_1-C_4$ | 2.8 |
| $C_5$ Hydrocarbons | 11.2 |
| $C_6-C_8$ Nonaromatics | 5.2 |
| Benzene | 45.9 |
| Toluene | 14.3 |
| Ethylbenzene and mixed xylenes | 10.3 |
| $C_9+$ Aromatics | 7.4 |

| Component | 6 Hrs. |
|---|---|
| Other $C_9+$ Hydrocarbons | 2.9 |

EXAMPLE 18

SAPO-5 was evaluated using the fractionated $C_9+$ feed of example 13. The procedure of example 11 was followed, except the feed rate was 0.64 grams of feed per gram of catalyst per hour and the average reactor temperature was 418° C. Analysis of the products at 6 hours gave the following:

| Component | 6 Hrs. |
|---|---|
| $C_1-C_4$ | 0.0 |
| $C_5$ Hydrocarbons | 20.4 |
| $C_6-C_8$ Nonaromatics | 5.9 |
| Benzene | 3.0 |
| Toluene | 1.3 |
| Ethylbenzene and mixed xylenes | 5.0 |
| $C_9+$ Aromatics | 48.3 |
| Other $C_9+$ Hydrocarbons | 16.1 |

We claim:

1. A low severity process for the preparation of a benzene-toluene-xylenes enriched stream containing minimal monoolefin and diolefin content, from a feed stream comprising a by-product effluent of a process for the pyrolitic cracking of hydrocarbons to produce light olefins or diolefins, said by-product effluent stream containing olefins and diolefins, said process comprising contacting said by-product effluent stream, under low severity conditions including a temperature within the range of about 300°–700° C., a pressure within the range of about 0 to 100 atmospheres, and a weight hourly space velocity within the range of about 0.1 to about 20, with a catalyst comprising a silicoaluminophosphate molecular sieve.

2. The process of claim 1 wherein the silicoaluminophosphate molecular sieve has a unit empirical formula on an anhydrous basis of:

$$mR:(Si_xAl_yP_z)O_2$$

wherein "R" represents at least one organic templating agent present in the intracrystalline pore system; "m" represents the moles of "R" present per mole of $(Si_xAl_yP_z)O_2$ and has a value from zero (0) to about 0.3, with the maximum value of m being related, at least in part, to the molecular dimensions of the template and the void volume of the intracrystalline pore system of the particular SAPO; "x", "y" and "z" represent the mole fractions of silicon, aluminum and phosphorus, respectively, present as tetrahedral oxide units, said mole fractions being within the pentagonal compositional area defined by points A, B, C, D and E of the ternary compositional diagram depicted by FIG. 1 of the drawings where the points A, B, C, D and E are represented by the following values for "x", "y" and "z":

| Point | Mole Fraction | | |
|---|---|---|---|
| | x | y | z |
| A | 0.01 | 0.47 | 0.52 |
| B | 0.94 | 0.01 | 0.05 |
| C | 0.98 | 0.01 | 0.01 |

-continued

| Point | Mole Fraction | | |
|---|---|---|---|
| | x | y | z |
| D | 0.39 | 0.60 | 0.01 |
| E | 0.01 | 0.60 | 0.39 |

3. The process of claim 2 wherein the silicoaluminophosphate has a minimum value for "m" of 0.02 in the as-synthesized form and have values for "x", "y" and "z" within the pentagonal compositional area defined by the points a, b, c, d and e of the ternary diagram which is FIG. 2 of the drawings, wherein said points a, b, c, d and e are represented by the following values for "x", "y" and "z":

| Point | Mole Fraction | | |
|---|---|---|---|
| | x | y | z |
| a | 0.02 | 0.49 | 0.49 |
| b | 0.25 | 0.37 | 0.38 |
| c | 0.25 | 0.48 | 0.27 |
| d | 0.13 | 0.60 | 0.27 |
| e | 0.02 | 0.60 | 0.38 |

4. Process of claim 1 wherein said conditions include a temperature within the range of about 350°–600° C., a pressure within the range of about 0–7 atmospheres, and a weight hourly space velocity within the range of about 0.5–5.0.

5. Process of claim 1 wherein said by-product effluent comprises a $C_4$ stream.

6. Process of claim 1 wherein said by-product effluent comprises a $C_5$ stream.

7. Process of claim 1 wherein said by-product effluent comprises a whole or fractionated dripolene stream.

8. Process of claim 1 wherein said feed stream is admixed with a diluent.

9. Process of claim 6 wherein said diluent is steam.

10. Process of claim 6 wherein said diluent is hydrogen.

11. Process of claim 6 wherein said diluent is a low boiling paraffin.

12. Process of claim 6 wherein said diluent is a mixture of a low boiling paraffin, hydrogen and/or steam.

13. Process of claim 2 wherein the silicoaluminophosphate is SAPO-11.

14. Process of claim 2 wherein the silicoaluminophosphate is SAPO-31.

15. Process of claim 2 wherein the silicoaluminophosphate is SAPO-5.

* * * * *